United States Patent
Heucher et al.

(10) Patent No.: US 10,800,956 B2
(45) Date of Patent: Oct. 13, 2020

(54) DEBONDABLE REACTIVE HOT MELT ADHESIVES

(71) Applicant: Henkel AG & Co. KGaA, Duesseldorf (DE)

(72) Inventors: Reimar Heucher, Pulheim (DE); Isabelle Ford, Maidenhead Berkshire (GB); Julie Joseph, Beaconsfield Buckinghamshire (GB); Alasdair Crawford, Hook Hampshire (GB)

(73) Assignee: Henkel AG & Co. KGaA, Duesseldorf (DE)

(*) Notice: Subject to any disclaimer, the term of this patent is extended or adjusted under 35 U.S.C. 154(b) by 0 days.

(21) Appl. No.: 15/674,581

(22) Filed: Aug. 11, 2017

(65) Prior Publication Data

US 2017/0355892 A1 Dec. 14, 2017

Related U.S. Application Data

(63) Continuation of application No. PCT/EP2016/054229, filed on Feb. 29, 2016.

(30) Foreign Application Priority Data

Feb. 27, 2015 (EP) .................................... 15157011

(51) Int. Cl.
| | |
|---|---|
| C09J 175/04 | (2006.01) |
| C09J 175/02 | (2006.01) |
| C09J 5/00 | (2006.01) |
| C07C 309/66 | (2006.01) |
| C08G 65/26 | (2006.01) |

(52) U.S. Cl.
CPC ........... *C09J 175/04* (2013.01); *C07C 309/66* (2013.01); *C09J 5/00* (2013.01); *C09J 175/02* (2013.01); *C08G 65/2615* (2013.01); *C09J 2301/502* (2020.08)

(58) Field of Classification Search
CPC ........ C09J 2205/302; C09J 175/04–08; C08G 18/10
See application file for complete search history.

(56) References Cited

U.S. PATENT DOCUMENTS

| | | | |
|---|---|---|---|
| 4,171,240 A | 10/1979 | Wong | |
| 4,729,797 A | 3/1988 | Linde et al. | |
| 5,100,494 A | 3/1992 | Schmidt | |
| 6,620,308 B2 | 9/2003 | Gilbert | |
| 7,332,218 B1 | 2/2008 | Gilbert | |
| 7,407,704 B2* | 8/2008 | Kirsten | C09J 5/02 156/711 |
| 8,796,389 B2* | 8/2014 | Prenzel | C09J 9/00 525/340 |
| 9,371,669 B2 | 6/2016 | Berg et al. | |
| 2004/0194881 A1* | 10/2004 | Hung | C08G 18/12 156/329 |
| 2006/0074214 A1* | 4/2006 | Kesselmayer | C08G 18/12 528/44 |
| 2007/0269659 A1 | 11/2007 | Gilbert | |
| 2008/0196828 A1 | 8/2008 | Gilbert | |
| 2009/0035580 A1* | 2/2009 | Chino | C08G 18/12 428/411.1 |
| 2009/0080932 A1* | 3/2009 | Mimura | G03G 15/0896 399/109 |
| 2010/0273008 A1* | 10/2010 | Burckhardt | C08G 18/10 428/423.1 |
| 2012/0171915 A1 | 7/2012 | Bartholomew et al. | |
| 2014/0374032 A1* | 12/2014 | Heucher | C09J 177/00 156/752 |
| 2015/0070743 A1* | 3/2015 | Branda | G02F 1/0063 359/241 |

FOREIGN PATENT DOCUMENTS

| | | |
|---|---|---|
| CN | 101238191 A | 8/2008 |
| DE | 102012203794 A1 | 9/2013 |
| EP | 1914285 A1 | 4/2008 |
| JP | 2010037355 A | 2/2010 |
| JP | 2011052056 A | 3/2011 |
| JP | 2013506063 A | 2/2013 |
| KR | 20150132919 A | 11/2015 |
| WO | 0105584 A1 | 1/2001 |
| WO | 2007142600 A1 | 12/2007 |
| WO | 2008150227 A1 | 12/2008 |
| WO | 2015016029 A1 | 2/2015 |

OTHER PUBLICATIONS

Machine Translation of JP 2010037355 (Year: 2020).*
International Search Report for International PCT Patent Application No. PCT/EP2016/054229 dated Jun. 2, 2016.

(Continued)

*Primary Examiner* — Michael M Dollinger
(74) *Attorney, Agent, or Firm* — James E. Piotrowski

(57) ABSTRACT

The present invention relates to a reactive hot melt adhesive composition, which at least partially loses its adhesiveness upon application of an electric voltage and thus allows debonding of substrates that have been bonded using said adhesive. Furthermore, the present invention relates to a method for its production and a method for forming a bonded substrate using such a reactive hot melt adhesive composition.

16 Claims, No Drawings

(56) References Cited

OTHER PUBLICATIONS

Lu et. al., A review of innovations in disbonding techniques for repair and recycling of automotive vehicles, International Journal of Adhesion and Adhesives, 2014, vol. 50, pp. 119-127.

M. Minnicino and J.M. Sands, Reactive nanocomposites for controllable adhesive debonding, Army Research Laboratory, Aug. 2011, report No. ARL-TR-5649.

S. Leijonmarck, Electrically induced adhesive debonding, Licentiate Thesis, 2010, ISBN 978-91-7415-815-1 KTH.

S. Leijonmarck et al., Electrolytically assisted debonding of adhesives: An experimental investigation, International Journal of Adhesion and Adhesives, 2012, pp. 39-45, vol. 32.

S. Leijonmarck et al., Electrochemical characterization of electrically induced adhesive debonding, Journal of the electrochemical society, 2011, vol. 158(10), pp. 109-114.

* cited by examiner

DEBONDABLE REACTIVE HOT MELT ADHESIVES

The present invention relates to a reactive hot melt adhesive composition, which at least partially loses its adhesiveness upon application of an electric voltage and thus allows debonding of substrates that have been bonded using said adhesive. Furthermore, the present invention relates to a method for its production and a method for forming a bonded substrate using such a reactive hot melt adhesive composition.

Adhesive bonds are commonly used in the assembly and finishing of manufactured goods. They are used in place of mechanical fasteners, such as screws, bolts and rivets, to provide bonds with reduced machining costs and greater adaptability in the manufacturing process. Adhesive bonds distribute stresses evenly, reduce the possibility of fatigue, and seal the joints from corrosive species. In many industrial applications hot melt adhesives are preferably used.

Hot melt adhesives are solid at room temperature but, upon application of heat, melt to a liquid or fluid state in which form they are applied to a substrate. On cooling, the adhesive regains its solid form. The hard phase(s) formed upon cooling the adhesive imparts all of the cohesion (strength, toughness, creep and heat resistance) to the final adhesive. Reactive hot melt adhesives, which are also applied in molten form, cool to solidify and subsequently cure by a chemical crosslinking reaction. An advantage of hot melt curable adhesives over traditional liquid curing adhesives is their ability to provide "green strength" upon cooling prior to cure. Advantages of reactive hot melt adhesives over non-reactive hot melt adhesives include improved temperature and chemical resistance.

The majority of reactive hot melts are moisture-curing urethane adhesives. These adhesives consist primarily of isocyanate terminated polyurethane prepolymers that react with surface or ambient moisture in order to chain-extend, forming a new polyurethane/urea polymer. Polyurethane prepolymers are conventionally obtained by reacting polyols with isocyanates. Cure is obtained through the diffusion of moisture from the atmosphere or the substrates into the adhesive, and subsequent reaction. The reaction of moisture with residual isocyanate forms carbamic acid. This acid is unstable, decomposing into an amine and carbon dioxide. The amine reacts rapidly with isocyanate to form a urea. The final adhesive product is a crosslinked material polymerized primarily through urea groups and urethane groups.

Additives are commonly included in reactive hot melt adhesive formulations. It is particularly advantageous to incorporate low cost additives that would provide improved properties, such as improved green strength before solidification and increased cure speed. Green strength before set is especially important for reactive hot melt adhesives because it enables the adhesive to yield handling bond strength immediately after application while maintaining desirable open and set times. Fast cure speed allows formulation components to be utilized more quickly. High green strength, long open times and fast cure speed are especially advantageous in certain moisture reactive hot melt adhesive end use applications, such as panel lamination and product assembly.

Hot melt adhesives are particularly advantageous for high-volume, low-cost manufacturing because of the simplicity of applying the adhesive to surfaces for bonding, the rapidity with which the adhesive bond is formed, and because a hot melt adhesive, while typically a mixture of materials, may be provided as a single component that does not require mixing or the addition of catalysts to initiate the chemical reaction forming an adhesive bond.

To separate the bond formed by a non-reactive hot melt adhesive, it is necessary to heat the bond to a temperature above the melting temperature of the adhesive. In practice, however, it is often impractical to apply sufficient heat to a large bonded assembly or to bonded parts that are thermally sensitive. Furthermore, molten adhesives typically retain substantial adhesive properties, such as a high degree of tack, which hinders separation and prevents clean surface separation. Instead, the molten adhesive separates by cohesive failure, leaving behind a stringy residue on the separated surfaces. Furthermore, in case a reactive hot melt adhesive is employed, it is generally not sufficient to apply heat to separate the bond, since the cured reactive hot melt adhesive can generally not be melted.

The ability to easily separate an adhesive bond, however, provides many benefits. Debonding, i.e., the release of an adhesive bond, may be desired when there is a need to disassemble a temporary structure or a previously bonded assembly of items, e.g., to allow repair, refurbishment, replacement or renovation operations. Simplified disbanding procedures also facilitate end-of-life recycling of materials and components from adhesively bonded goods and structures. Moreover, reversible bonding is beneficial for packaging or for use in securing items during shipping.

The separation strategies that do exist typically involve time-consuming chemical procedures requiring high temperatures and aggressive chemicals. Examples of such techniques are described in U.S. Pat. No. 4,171,240 to Wong and U.S. Pat. No. 4,729,797 to Linde et al. These techniques, although generally effective, are quite harsh and can damage the objects being separated, making them unsuitable for many applications.

To provide materials that are more easily removed from a substrate, the prior art describes adhesives formed from reactive monomers containing linkages susceptible to chemical degradation, e.g., curable resins containing thermally labile linkages or thermally reversible crosslinks. Although these specially prepared materials are more readily cleaved from the substrate, they still require conditions that are harsh to delicate substrates or adjacent adhesive bonds.

Adhesives that are electrically debondable and contain ionic components are known as well as various ionic liquids that can generate conductivity in solids. For example, DE 102012 203 794 A1 describes a hot melt adhesive based on polyamides that contains ionic electrically conductive components that is debondable upon application of an electric voltage. However, debondable reactive hot melt adhesives are not disclosed.

Thus, there still remains the need in the art for improved adhesives, in particular adhesives that provide "green strength" upon cooling, have an improved temperature as well as chemical resistance and which can be debonded selectively and precisely under mild conditions, ideally from both bonded surfaces. Such a material would provide adhesive bonds that could be employed in a variety of applications where facile removal of the material from the surface is desired and additionally provide all the advantages of a reactive hot melt adhesive.

The inventors have now surprisingly found that this need can be met by reactive hot melt adhesives that contain organic or inorganic salts and therefore become debondable upon application of an electric voltage. This is even more surprising, since the storage stability and curing speed is not detrimentally affected.

In a first aspect, the present invention thus relates to an electrically debondable reactive hot melt adhesive composition, comprising:
- a) at least one isocyanate-functional polyurethane polymer; and
- b) at least one organic or inorganic salt.

In another aspect, the present invention relates to a method for producing an electrically debondable reactive hot melt adhesive composition according to the present invention, the method comprising blending of a reactive polyurethane hot melt in a molten state with the at least one organic or inorganic salt, wherein the reactive polyurethane hot melt comprises the isocyanate-functional polyurethane polymer and optionally one or more additives, wherein the blending is performed at temperatures such as to keep the hot melt in the molten state.

In still another aspect, the present invention relates to a method forming a debondable adhesive bond between a first and a second substrate, the method comprising the steps of:
- a) applying the electrically debondable reactive hot melt adhesive composition according to any one of claims 1 to 9 to the surface of the first substrate and optionally the surface of the second substrate;
- b) contacting the first and the second substrates such that the electrically debondable reactive hot melt adhesive composition is interposed between the two substrates;
- c) allowing formation of an adhesive bond between the two substrates to provide bonded substrates; and
- d) optionally applying a voltage to the bonded substrates whereby adhesion at at least one interface between the electrically debondable reactive hot melt adhesive composition and a substrate surface is substantially weakened.

In a still further embodiment, the present invention relates to a bonded substrate obtained according to the methods described herein that can be debonded upon application of an electric voltage and, optionally, heat.

Further preferred embodiments are set out in the dependent claims.

"One or more", as used herein, relates to at least one and comprises 1, 2, 3, 4, 5, 6, 7, 8, 9 or more of the referenced species. Similarly, "at least one" means one or more, i.e. 1, 2, 3, 4, 5, 6, 7, 8, 9 or more. "At least one", as used herein in relation to any component, refers to the number of chemically different molecules, i.e. to the number of different types of the referenced species, but not to the total number of molecules. For example, "at least one polyol" means that at least one type of molecule falling within the definition for a polyol is used but that also two or more different molecule types falling within this definition can be present, but does not mean that only one molecule of said polyol is present. In the present specification the terms "a" and "an" and "at least one" are the same as the term "one or more" and can be employed interchangeably.

If reference is made herein to a molecular weight, this refers to the average number molecular weight $M_n$, if not explicitly stated otherwise. The number average molecular weight $M_n$ can be calculated based on end group analysis (OH numbers according to DIN EN ISO 4629) and the functionality of the compound or can be determined by gel permeation chromatography according to DIN 55672, in particular DIN 55672-1 with THF as the eluent. If not stated otherwise, all given molecular weights are those determined by gel permeation chromatography according to DIN 55672-1 with THF as the eluent. The weight average molecular weight $M_w$ can be determined by GPC, as described for $M_n$.

In the present description, the isocyanate content, also referred to as NCO content or isocyanate value, refers to a value as determined according to DIN EN ISO 11909, if not stated explicitly otherwise.

If reference is made herein to a hydroxy value (OH value, OH number), this refers to a value as determined according to DIN EN ISO 4629, if not stated explicitly otherwise.

Based on the hydroxyl value and the NCO content the NCO/OH equivalent ratio can be calculated.

In the present description, the melting point refers to a value measured by differential scanning calorimeter (DSC) according to ISO 11357, in particular ISO 11357-3, if not stated otherwise. Specifically, a peak top of an endothermic peak observed when the temperature is raised from −50° C. to 250° C. at a rate of 10° C./minute was regarded as the melting temperature.

If reference is made herein to a softening point, this refers to a value measured by differential scanning calorimeter (DSC) according to ISO 11357, in particular ISO 11357-3, if not stated otherwise. Specifically, a peak top of an endothermic peak observed when the temperature is raised from −50° C. to 250° C. at a rate of 10° C./minute was regarded as the softening point.

All percentages given herein in relation to the compositions or formulations relate to % by weight (wt. %) relative to the total weight of the respective composition or formulation, if not explicitly stated otherwise.

"About" or "approximately" as used herein in connection with a numerical value refers to the numerical value ±10%, preferably ±5%. "About 20% by weight" thus relates to 20±2, preferably 20±1% by weight.

The electrochemically debondable compositions of the invention possess matrix functionality and electrolyte functionality. The electrolyte functionality provides sufficient ionic conductivity to support a faradaic reaction at an electrically conductive substrate surface in contact with the composition. This electrolyte functionality is achieved by using an organic or inorganic salt. The matrix functionality of the debondable composition provides the adhesive properties needed for its intended use. This matrix functionality is achieved by the at least one isocyanate-functional polyurethane polymer.

The adhesiveness of the composition is weakened by the application of an electrical voltage across the bondline between the composition and at least one surface to which it is bonded. While not wishing to be bound to any particular theory concerning the mode of operation, it is assumed that the faradaic reaction, which takes place at the composition/substrate interface, weakens the bond therebetween. While the faradaic reaction may cause debonding directly, the weakening of the adhesive bond may be the result of an indirect process initiated by the faradaic reaction, in particular the free flow of ions, which destabilizes the morphology of the polymer used to form the adhesive.

According to the present invention the matrix functionality is provided by polyurethane polymers such as those typically used in reactive hot melt adhesives. The materials may be prepared from commercially available polyurethane polymer resins, often without modification. Accordingly, the terms "polyurethane", "polyurethane polymer", "polyurethane resin" are used interchangeably herein to relate to isocyanate-functional polyurethane polymers, such as those typically used in reactive hot melt applications.

The polyurethane provides the adhesive composition with the necessary adhesive properties, including tack, adhesiveness, cohesiveness, melt characteristics and stability. These basic properties may optionally be controlled by additives and auxiliaries, commonly used and known to those skilled in the art.

The polyurethanes described herein are isocyanate-functional polyurethane prepolymers, also referred to as NCO-functional polyurethane prepolymers. "NCO", as used herein, refers to the isocyanate group —N=C=O. The polyurethane of the invention is obtainable by reacting at least one polyol with at least one polyisocyanate, wherein the at least one polyisocyanate is used in an amount such that NCO groups are present in molar excess relative to the hydroxyl groups of the at least one polyol. Consequently, the NCO/OH equivalent ratio is more than 1, preferably between 1 and 2, more preferably between 1.2 and 1.8. The free NCO content is typically in the range from 0.1 to 5% by weight of the polyurethane prepolymer, preferably 1 to 2.5% by weight.

In various embodiments, the polyols used for the production of the polyurethanes may be selected from those typically used in the field, including, without limitation, polyether polyols, polyester polyols, polycarbonate polyols, polyacetal polyols, polyamide polyols, polyesteramide polyols, polyalkylene polyether polyols, polythioether polyols and mixtures thereof, preferably polyether polyols, polyester polyols, polycarbonate polyols and mixtures thereof.

Polyester polyols include those that are obtainable by reacting, in a polycondensation reaction, dicarboxylic acids with polyols. The dicarboxylic acids may be aliphatic, cycloaliphatic or aromatic and/or their derivatives such as anhydrides, esters or acid chlorides. Specific examples of these are succinic acid, glutaric acid, adipic acid, pimelic acid, suberic acid, azelaic acid or sebacic acid, phthalic acid, terephthalic acid, isophthalic acid, trimellitic acid, phthalic acid anhydride, tetrahydrophthalic acid anhydride, glutaric acid anhydride, maleic acid, maleic acid anhydride, fumaric acid, dimeric fatty acid and dimethyl terephthalate. Examples of suitable polyols are monoethylene glycol, 1,2-propanediol, 1,3-propanediol, 1,4-butanediol, 3-methyl-pentane-1,5-diol, neopentyl glycol (2,2-dimethyl-1,3-propanediol), 1,6-hexanediol, 1,8-otaneglycol cyclohexanedimethanol, 2-methylpropane-1,3-diol, diethyleneglycol, triethyleneglycol, tetraethyleneglycol, polyethyleneglycol, dipropyleneglycol, tripropyleneglycol, tetrapropyleneglycol, polypropyleneglycol, dibutyleneglycol, tributyleneglycol, tetrabutyleneglycol and polybutyleneglycol. Alternatively, they may be obtained by ring-opening polymerization of cyclic esters, preferably ε-caprolactone.

In various embodiments, the polyester polyol has a melting temperature $T_m$ >0° C., preferably >40° C. and/or has an average number molecular weight $M_n$ in the range of 400 to 5,000, preferably 400 to 3,000 g/mol, more preferably 800 to 2,500 g/mol, most preferably 1,000 to 2,000 g/mol.

Polyether polyols include polyalkylene glycol homo- or copolymers, in particular polypropylene glycol homo- or copolymers, polyethylene glycol homo- or copolymers, polytetramethylene glycol homo- or copolymers, or polypropylene glycol/polyethylene glycol block copolymers.

In various embodiments, the polyether polyol has an average number molecular weight of 1,000 to 4,000, preferably 1,000 to 3,000 g/mol.

Suitable polycarbonate polyols can be obtained by reaction of carbon acid derivatives, e.g. diphenyl carbonate, dimethyl carbonate or phosgene with diols. Suitable examples of such diols include ethylene glycol, 1,2- and 1,3-propanediol, 1,3- and 1,4-butanediol, 1,6-hexanediol, 1,8-octanediol, neopentyl glycol, 1,4-bishydroxymethyl cyclohexane, 2-methyl-1,3-pro-panediol, 2,2,4-trimethyl pentanediol-1,3, dipropylene glycol, polypropylene glycols, dibutylene glycol, polybutylene glycols, bisphenol A, bisphenol F, tetrabromobisphenol A as well as lactone-modified diols. The diol component preferably contains 40 to 100 wt % hexanediol, preferably 1,6-hexanediol and/or hexanediol derivatives. More preferably the diol component includes examples that in addition to terminal OH groups display ether or ester groups.

The polycarbonate polyols should be substantially linear. However, they can optionally be slightly branched by the incorporation of polyfunctional components, in particular low-molecular polyols. Suitable examples include glycerol, trimethylol propane, hexanetriol-1,2,6, butanetriol-1,2,4, trimethylol propane, pentaerythritol, quinitol, mannitol, and sorbitol, methyl glycoside, 1,3,4,6-dianhydrohexites.

Suitable polycarbonate polyols are, without limitation, those obtainable under the trademark names Desmophen® C3200 (Bayer) and Kuraray® C2050 (Poly-(3-methyl-1,5-pentanediol, 1,6-hexanediol)carbonate; Kuraray).

In addition further polyols, in particular diols, may be used in combination with the above. Such diols may be monomeric diols, such as 1,4-butanediol.

Suitable polyols further comprise polyols that are hydroxy-functionalized polymers, for example hydroxy-functionalized siloxanes as well as polyols that comprise additional functional groups, such as vinyl or amino groups.

For use as the polyisocyanate any compound which includes at least two isocyanate groups is within the contemplation of the present invention. It is preferable, however, that the polyisocyanate be a diisocyanate. The incorporation of small amounts of isocyanate with a functionality higher than two, in particular a triisocyanate, is also contemplated and may under certain circumstances even be advantageous. Such polyisocyanates can act as cross-linkers. In this case where the polyisocyanate acts as a cross-linker, polyisocyanates based on hexamethylene diisocyanate are preferred. Suitable diisocyanates include, without limitation, methylenediphenyl diisocyanate (MDI), toluene-2,4-diisocyanate (TDI), hexamethylene diisocyanate (HDI), polymeric diphenylmethane diisocyanate (PMDI), isophorone diisocyanate (IPDI), methylene-4,4-bis(cyclohexyl)diisocyanate (H12MDI) and mixtures thereof. Although both aliphatic and aromatic polyisocyanates are within the contemplation of the present invention, it is preferred that the polyisocyanate be an aliphatic polyisocyanate. Thus, in a particularly preferred embodiment, the polyisocyanate is an aliphatic diisocyanate. Among particularly preferred aliphatic diisocyanates are isophorone diisocyanate, hexamethylene diisocyanate, and mixtures thereof. Suitable polyisocyanates are, for example, commercially available under the trademark name Desmodur® from Bayer AG (DE). The use of aliphatic isocyanates has the advantage that the resulting isocyanate-functional polyurethane polymer is less reactive towards the organic or inorganic salt or further compounds such as polar compounds used a solvating matrix or additives. This will provide electrically debondable reactive hot melt adhesive composition with improved storage stability.

The polyurethane may also be a hybrid polymer and may, in addition to the urethane units, comprise additional polymeric units, such as acrylates, siloxanes and the like.

Generally, the components used for synthesis of the polyurethane are selected such that meltable, non-cross-linked products are obtained. The type of polyols and isocyanates used, in particular the polyols used, are decisive for the melting behavior and the viscosity of the molten polymer.

In various embodiments, the molecular weight $M_w$ of the polyurethane is between 10,000 and 250,000 g/mol, preferably 50,000 to 150,000 g/mol.

In the molten state, the polyurethane should have a viscosity of between 1,000 and 100,000 mPas (as measured at 100° C., Brookfield Thermosel RVT, EN ISO 2555), preferably 2,000 to 50,000 mPas, more preferably 3,000 to 10,000 mPas. The softening point of a suitable polyurethane should preferably be between 60° C. and 220° C., in particular 80° C. to 120° C.

In various embodiments, the polyurethane is used in amounts of about 20 to about 90% by weight of the adhesive composition, preferably 40 to 90% by weight.

The polyurethanes can be combined with commonly known additives and auxiliaries to prepare the hot melt adhesives. These include, without limitation, plasticizers, adhesion promoters, pigments, leveling agents, gloss promoters, stability enhancers, anti-foaming agents, antioxidants and fillers. Plasticizers increase the plasticity of the compositions; for example, polar plasticizers such as esters, long-chain amines, sulfonic esters are usable. Fillers can furthermore be used in subordinate quantities, for example silicates, talc, calcium carbonates, clays, carbon black, or color pastes or pigments. Electrically conductive pigments and fillers are preferably not to be used. The reactive hot melt adhesive may further include particles of a non-conducting material, e.g., crushed glass or plastic beads, to prevent conductive surfaces used from contacting each other in the debonding process and forming a short circuit. Other additives will be apparent to those skilled in the art and are within the scope of the invention.

The hot melt composition may further comprise additional polymers that are suited for hot melt applications, including polyamides, polyacrylates and polyesters. However, if these are used, they are used in amounts of only up to 30% by weight relative to the amount of the polyurethane.

The above polymers are well suited to provide the matrix functionality of the composition. However, in order to support a faradaic reaction at an electrically conductive substrate, the debonding composition also must possess sufficient ion conductivity to permit ion transport. Therefore, the electrically debondable adhesive composition further includes an organic or inorganic salt to provide the electrolyte functionality of the debondable adhesive composition. The organic or inorganic salts can be solid or liquid at 25° C. and 1013 mbar, i.e. the salts include solid salts as well as the so-called ionic liquids.

The organic or inorganic salts may be dissolved or dispersed in the polyurethane or they may be associated with polymer groups.

In the following, ionic or neutral compounds are enumerated, but it should be understood that this refers to the corresponding ionic structures present in the salts. It is also possible that said salts contain water of crystallization in bound form.

For example, salts of organic acids may be used, such as, for example, Li, Na or K salts of aliphatic $C_{2-6}$ mono- or di-carboxylic acids, aromatic mono- or di-carboxylic acids, and trifluoromethane sulfonic acids. In one embodiment, a quaternary organic compounds is used as a cation, with the anion being the afore-mentioned acid anions or halides. A further preferred embodiment uses as an anion organic compounds containing sulfone groups, either as part of a cyclic structure, such as acesulfames or saccharinates, as part of a linear structure, such as trifluoromethanesulfonate, bis(trifluoromethane sulfonyl)imide or trifluoromethane carbonyl-trifluoromethane sulfonyl imide.

Cationic quaternary organic compounds that may be used include, without limitation, tetraalkylphosphonium, trialkylsulfonium, tetraalkylammonium, $N^+$-alkyl-substituted cyclic 5- or 6-membered ring amines, $N^+$-alkyl substituted aromatic 5-membered ring imidazolines, wherein the alkyl group may be an linear aliphatic alkyl radical with 1 to 12 carbon atoms. The alkyl radicals may be the same or different and can optionally also be substituted with an OH group.

In principle, the various anions and cations can be combined with each other as long as the compounds obtained have salt-like properties. In a preferred embodiment, the salt-like compound should have a melting temperature above 40° C. It is also preferred that the organic or inorganic salt does not react with the isocyanate functional polyurethane polymer or with atmospheric water.

Examples of suitable cationic groups include, without limitation, tetraalkyl-substituted N-compounds, such as N-tetrabutyl-ammonium, N-trimethyl-N-butyl ammonium, N-triethyl-N-benzylammonium, N,N-dimethyl-cyclohexylamine, N-methyl-N-trioctylammonium; OH-functionalized tetraalkylamines, such as trimethyl-hydroxyethylammonium (choline), acetylcholine, N-methyl-N-hydroxyethyl-cyclohexylamine; Trialkyl-substituted S-compounds, such as triethylsulfonium, trimethylsulfonium; 5-membered N-heterocycles, such as N-alkyl imidazolium derivatives, such as 1-methyl-3-ethyl-imidazolium, 1-ethyl-3-methyl-imidazolium, 1-butyl-3-methylimidazolium, 1-hexadecyl-3 methyl-imidazolium, 1-methyl-3-octyl-imidazolium, 1-methyl-3-nonyl-imidazolium, 1-heptyl-3-methyl-imidazolium, 1-ethyl-2-methyl-imidazolium, 1-propyl-4-methyl-imidazolium, 1-propyl-2-methyl-imidazolium, 1,2-dimethyl-3-propyl-imidazolium; 6-membered N-heterocycles, for example, alkyl-substituted pyridinium, pyrrolidinium, or piperidinium compounds, such as 1-butyl-pyridinium, 1-butyl-3-methyl-pyridinium, 1-butyl-4-methyl-pyridinium, 1-propyl-3-methyl-pyridinium, 1-butyl-3-propyl-piperidinium, 1-butyl-1-methylpyrrolidinium, 1-butyl-3-methyl-pyrrolidinium, 1-hexyl-3-methyl-pyrrolidinium, and the like.

It is preferable for some applications to avoid halides as anions. Examples of suitable anions include, without limitation, tetrafluoroborate, trifluoromethane sulfonate, aromatic dicarboxylates such as phthalic acid and its isomers, sulfonate group containing compounds, such acesulfams, saccharinates, bis(trifluoromethane sulfonyl)imide or trifluoromethane carbonyl-trifluoromethane sulfonyl imide.

Preferred are trifluoromethane sulfonate salts, in particular the alkali metal salts, more particular lithium trifluoromethane sulfonate.

The organic or inorganic salt is included in the debondable adhesive composition in an amount sufficient to provide the requisite ionic conductivity to support the faradaic reaction of the debonding process. The actual amount of organic or inorganic salt used in a particular composition is dependent on the ionic conductivity of the polymer and the ability of the salt to form a continuous conductive pathway within the composition. While a continuous pathway is not absolutely required, it promotes the efficiency of the process. Where ions are required to tunnel through regions of higher resistance, higher voltages and longer times are required for debonding.

In the adhesive compositions according to the present invention, at least one organic or inorganic salt is typically used in an amount of 1 to 30%, preferably in an amount of 1 to 16% by weight of the adhesive composition.

As a further component, the reactive hot melt adhesive composition preferably comprises at least one polar compound which is different from the at least one isocyanate-functional polyurethane polymer and the at least one organic or inorganic salt. The polar compound is also referred to as "solvating matrix" herein. Such polar compounds can promote miscibility with the salts. The salt and the solvating matrix may form a suspension, dispersion or solution. Preferably, the salts remain within the solvating matrix. This improves structural and chemical integrity of the adhesive whilst when put under applied voltage the salt is able to migrate through the matrix. The polar compounds can include polymers, such as polyphosphazenes, polymethylenesulfides, polyoxyalkylene glycols, polyethylene imines, polyethylene amines and the like. Also suitable are low molecular weight polyols. These compounds may be solid or liquid at 25° C. and 1013 mbar.

A group of suitable polar compounds include low molecular weight aliphatic polyols with 2 to 120 hydroxyl groups. These typically have a molecular weight of up to 1,000 g/mol, preferably up to 500 g/mol. Preferred are those having 3 to 6 OH groups. Examples include, without limitation, neopentyl glycol, pentaerythritol, glycerol, monosaccharides and sugar alcohols, such as glucose, arabinose, xylose, mannitol, sorbitol, arabinose and other multiple OH-groups containing compounds.

In a preferred embodiment the polar compound has only up to one H-acidic functional group. An H-acidic functional group is an NCO-reactive functional group and may be a primary amino group, a secondary amino group, a mercapto group, a carboxyl group or a hydroxyl group. The use of a polar compound with one H-acidic functional group or less may prevent the electrically debondable reactive hot melt adhesive composition from premature curing before its application. Most preferably, the polar compound does not contain H-acidic functional groups, i.e. most preferably the polar compound is an aprotic polar compound. This is to ensure, that the polar compound does not detrimentally affect the storage stability and the reactivity of the electrically debondable reactive hot melt adhesive composition.

A group of suitable polar compounds include polyethers, in particular polyethylene glycols and polypropylene glycols. Particularly suitable are end-capped polyethers, i.e. reaction products of polyether polyols in which hydroxyl groups have been reacted such that the polyethers contain only up to one H-acidic functional group, preferably no H-acidic functional group. Such polyethers are commercially available. Particularly suitable are polyethers, preferably end-capped polyethers, with a molecular weight below 10,000 g/mol preferably from 350 to 5,000 g/mol. These polyethers may be solid or liquid at 25° C. and 1013 mbar.

Suitable end-capped polyethers are allyl alcohol ethoxylate, methyl end capped; allyl alcohol ethoxylate propoxylate, methyl end capped (EO/PO random); allyl alcohol ethoxylate, allyl end capped; allyl alcohol ethoxylate propoxylate, allyl end capped (EO/PO random); allyl alcohol ethoxylate, epoxy group end capped; allyl alcohol ethoxylate propoxylate, epoxy group end capped (EO/PO random); allyl alcohol ethoxylate propoxylate, butyl end capped (EO/PO random); allyl alcohol ethoxylate, acetyl end capped; allyl alcohol ethoxylate propoxylate, acetyl end capped (EO/PO random); methyl alcohol ethoxylate, epoxy group end capped; methyl alcohol ethoxylate propoxylate, epoxy group end capped; butyl alcohol ethoxylate, epoxy group end capped; butyl alcohol ethoxylate propoxylate, epoxy group end capped (EO/PO random); fatty alcohol polyoxyethylene ether, methyl end capped; fatty alcohol polyoxyethylene ether, butyl end capped; nonyl phenol polyoxyethylene ether, butyl end capped; poly(ethylene glycol) di methyl ether; poly(ethylene glycol) methyl ether methacrylate; poly(ethylene glycol) methyl ether; poly(ethylene glycol) methyl ether acrylate; poly(ethylene glycol) methyl ether acrylate; Poly(ethylene glycol) diglycidyl ether; poly(ethylene glycol) dimethyl ether; poly(ethylene glycol) ethyl ether methacrylate; poly(ethylene glycol) dimethacrylate; poly(ethylene glycol) divinyl ether; poly (ethylene glycol) butyl ether; poly(ethylene glycol) methyl ether tosylate; poly(ethylene glycol) behenyl ether methacrylate solution; poly(ethylene glycol) methyl ether tosylate; poly(ethylene glycol) tetrahydrofurfuryl ether; poly (ethylene glycol) octyl ether; poly(ethylene glycol) phenyl ether acrylate; polyethylene glycol-bis(2-ethylhexanoate) (PEG-bis(2EH)) and mixtures thereof. Particularly suitable is polyethylene glycol-bis(2-ethylhexanoate).

Also suitable are, for example, cyclic carbonates, such as 1,3-dioxolan-2-ones, preferably with a molecular weight of below 1000 g/mol, more preferably below 500 g/mol, yet more preferably below 200 g/mol.

Suitable cyclic carbonates include 4-Fluoro-1,3-dioxolan-2-one, 4-Chloro-1,3-dioxolane-2-one, 4,5-dichloro-1,3-dioxolan-2-one, 4-Vinyl-1,3-dioxolan-2-one, 4-ethyl-1,3-dioxolan-2-one, 4,4-dimethyl-5-methylene-1,3-dioxolan-2-one, 4-Ethyl-1,3-dioxolan-2-one (1,2-butylene carbonate), cis-4,5-Dimethyl-1,3-dioxolan-2-one (cis-2,3-butylene carbonate), 1,3-dioxolan-2-one (ethylene carbonate) and 4-methyl-1,3-dioxolan-2-one (propylene carbonate).

Particularly suitable cyclic carbonates are ethylene carbonate, propylene carbonate and mixtures thereof.

Dimethyl sulfoxide (DMSO) and N,N-Dimethylformamide (DMF) may also be employed as the at least one polar compound.

In a preferred embodiment according to the present invention, the solvating matrix is formed by propylene carbonate or ethylene carbonate and the organic or inorganic salt is lithium trifluoromethanesulfonate.

In another preferred embodiment, the solvating matrix is formed by poly(ethylene glycol)bis(2-ethylhexanoate) and the organic or inorganic salt is lithium trifluoromethanesulfonate.

The polar compounds may be used individually or in combination. In various embodiments, the polar compounds used are liquid at 25° C. and 1013 mbar or have a melting temperature below the melting temperature of the adhesive, preferably below 100° C., more preferably below 80° C., even more preferably below 60° C.

The polar compounds can be used in amounts from 0 to 25% by weight, preferably 5 to 15% by weight, based on the total weight of the hot melt adhesive.

The electrolyte functionality of the debondable composition provides ionic conductivity sufficient to maintain a faradaic reaction at an interface with an electrically conductive surface. Sufficient conductivity may be readily established by preparing a composition and applying a voltage across a bondline with an electrically conductive substrate. If current flow is observed, a faradaic reaction at the bondline may be assumed. Sufficient ionic conductivity also may be empirically observed by applying a voltage across the bondline and noting whether the bond is weakened. Compositions with ionic conductivities in the range of $10^{-11}$ to $10^{-3}$ S/cm at room-temperature are considered within the scope of the invention. Materials having higher ionic conductivities generally require shorter debonding times. Compositions with ionic conductivities in the range of $10^{-9}$ to $10^{-7}$ S/cm at room-temperature are preferred.

Methods for producing a reactive hot melt adhesive composition as described herein are known in the art. Such methods may include adding additives and auxiliaries to the polyurethane in molten state using the known devices, such as static mixers, dissolvers, kneaders and extruders. The adhesive is then cooled and can be stored. In various embodiments according to the present invention, the method comprises blending of a reactive polyurethane hot melt with the organic or inorganic salt and optionally one or more additives, wherein the blending is performed at a temperature such as to keep the composition in the molten state.

A bonded substrate may be obtained by disposing a debondable composition as described herein between two or more surfaces of two or more substrates such that the composition forms an adhesive bond to each surface and holds each surface in a generally fixed position relative to the other surface or surfaces while maintaining those positions in response to a force equal to at least the weight of the lightest bonded element.

The reactive hot melt adhesive of the invention typically has a softening point of 80 to 220° C. It is typically melted at temperatures of for example up to 220° C., preferably 80 to 120° C., and then applied in a flowable state to a substrate. The viscosity of a hot melt adhesive of the invention may preferably range from 500 to 25,000 mPas at an application temperature of 80° C. to 120° C. (Brookfield Thermosel RVT, EN ISO 2555). The viscosity can be adapted to the method of application. It is known to reduce a high viscosity by raising the temperature. Immediately afterwards, the second substrate is pressed against the adhesive layer and, after cooling, a physical adhesive bond is formed. Those skilled in the art are familiar with devices for melting and application of hot melt adhesives. The thickness of the adhesive layer is also known to the skilled person, and it can be chosen based on his technical knowledge and the desired application. The layer thickness is usually from 5 to 1,000 µm, in particular from 10 to 500 µm. After cooling, the solidified layer provides the adhesive bond. The adhesive layers may be amorphous, but they may also have crystalline constituents.

The methods for forming a debondable adhesive bond between a first and a second substrate using the described compositions thus usually involve the steps of:
i) applying the electrically debondable reactive hot melt adhesive composition according to the invention to the surface of the first substrate and optionally the surface of the second substrate;
ii) contacting the first and the second substrates such that the electrically debondable reactive hot melt adhesive composition is interposed between the two substrates;
iii) allowing formation of an adhesive bond between the two substrates to provide bonded substrates; and
iv) optionally applying a voltage to the bonded substrates whereby adhesion at least one interface between the electrically debondable reactive hot melt adhesive composition and a substrate surface is substantially weakened.

The "substrate", in the context of the present invention, to which a reactive hot melt adhesive composition according to the present invention may be applied, may be any kind of substrate, including plastics, metals, ceramics and other substrates. Preferably, the substrates are cleaned on the surface to be bonded. It is also optionally possible for additional primer layers or other coatings to be applied. The substrates may be solid and rigid but in other embodiments, flexible substrates, such as one layer or multilayer films may be used for bonding. The two substrates may be made of the same or of different materials.

It is preferred that the substrates used for bonding, or at least one of them, is electrically conductive or has an electrically conductive surface such that an electric voltage may be applied in order to weaken the bond formed by the adhesive composition. This can be achieved by way of a conductivity of the substrate itself, the substrate can have a conductive coating or, for example, electrically conductive constituents are incorporated into the substrate. Examples for suitable electrically conductive substrates include metal substrates, such as, without limitation, aluminum, steel, zinc, etc. as well as alloys and mixtures thereof. The hot melt adhesives according to the present invention are particularly suitable for adhesively bonding metallic substrates or plastic substrates.

The debonding according to the invention can be achieved by applying an electric voltage to the bonded substrates. For this purpose, typically perpendicular to the adhesive layer, that is to say in the direction from one substrate to another substrate, an electrical voltage is applied. The voltage typically ranges from 9 to 100 V, especially 9 to 48 V. Particularly suitable is a DC voltage.

After a certain reaction time, the two substrates can be detached from each other by at normal traction or lateral shearing. The speed of adhesion loss can be influenced by the amount and type of salts. If a fast separation is desired, for example 10 to 60 sec., the amount can be increased. If a fast loss of adhesion is not desired, for example 2 to 5 min, a lesser amount is sufficient. Typically, the time period for which the voltage is applied, may range from 1 second to 20 minutes, in particular from 1 second to 3 minutes.

The debonding of the adhesive composition and the surfaces according to the present invention may be triggered by only one stimulus, this stimulus being an electrical stimulus. Exposure to said electrical current may be conducted at ambient temperatures, that is, for example, at room temperature around 20° C. Additionally, in order to facilitate the debonding process, a second stimulus may be applied. This second stimulus may be heat. The combination of an electrical current and elevated temperatures results in even easier debonding. However, heat exposure is optional.

Accordingly, in various other embodiments, the adhesive layer may additionally be heated for the debonding. In particular, heating at up to 80° C. is advantageous, in particular from 35 to 70° C. This temperature is not sufficient to make the adhesive flowable, but together with the applied voltage only leads to a loss of adhesion. The increased temperature may also affect the polar compounds if they are used and have melting temperatures within this temperature range. The melting of the polar compounds may support the debonding process. It is also possible at heat can increase the mobility of the matrix, the polar compound, an in particular the organic or inorganic salt. A debonding mechanism which is triggered by heat together with voltage is referred to as dual trigger debonding, while the application of voltage alone is referred to as single trigger debonding.

Methods for heating the substrates and/or adhesive layer for debonding are known to those skilled in the art and include, without limitation, hot gas exposure, such as hot air exposure, and exposure to radiation sources, such as IR or NIR radiation. It is also possible to heat the adhesive layer by ultrasound.

It is understood that all embodiments disclosed herein in relation to the compositions are similarly applicable to the disclosed methods and uses and vice versa.

The following examples are given to illustrate the present invention. Because these examples are given for illustrative purposes only, the invention should not be deemed limited thereto.

EXAMPLES

Preparation of the Electrically Debondable Reactive Hot Melt Adhesive Compositions Reactive polyurethane hot melts were heated to 70° C. Subsequently an electrolyte composition was added in appropriate amounts, followed by mechanical agitation (70 rpm) for approximately 10 minutes. The heat applied has to be sufficient enough to maintain the composition in a molten state, whilst the mechanical agitation is required to disperse the ionic material thoroughly to achieve visual homogeneity.

Example 1

An electrically debondable reactive polyurethane hot melt composition, comprising an isocyanate-functional polyurethane polymer with a free NCO content of ca. 1.8% and containing 15 wt % electrolyte composition 1 was applied between two aluminum substrates to form a composite. Electrolyte composition 1=30 wt. % lithium trifluoromethanesulfonate ($CF_3SO_3Li$) 70 wt % 4-Methyl-1,3-dioxolan-2-one (propylene carbonate) ($C_4H_6O_3$)

Upon introduction of 48 V current at 25 ° C. and 1 atm, adhesive failure observed at cathode attached substrate with bond strengths of 0.06 MPa (control=1.15 MPa). Upon introduction of 48 V current at 45° C. and 1 atm, adhesive failure observed at cathode attached substrate with bond strengths of 0.63 MPa (control=1.10 MPa). Upon introduction of 48 V current at 65° C. and 1 atm, adhesive failure is observed at cathode attached substrate with bond strengths of 0.30 MPA (control=0.58 MPA).

Example 2

The electrically debondable reactive polyurethane hot melt composition from Example 1 was applied between one aluminum substrate and one stainless steel substrate to form composite.

Upon introduction of 48 V current at 25° C. and 1 atm, adhesive failure was observed at the cathode attached substrate with bond strengths of 0.05 MPa.

Example 3

The electrically debondable reactive polyurethane hot melt composition from Example 1 was applied between two aluminum substrates to form a composite.

Upon introduction of 9 V current at 25° C. and 1 atm, adhesive failure observed at cathode attached substrate with bond strengths of 0.04 MPa (control=1.15 MPa).

Example 4

An electrically debondable reactive polyurethane hot melt composition comprising the isocyanate-functional polyurethane polymer with a free NCO content of ca. 1.8% and containing 15 wt % electrolyte composition 2, as defined below, was applied between two aluminum substrates to form a composite.

Electrolyte composition 2=30 wt. % lithium trifluoromethanesulfonate ($CF_3SO_3Li$) 70 wt. % poly(ethylene glycol)bis (2-ethylhexanoate) (PEG-bis-2EH) average $M_N$~650

Upon introduction of 48 V current at 25° C. and 1 atm, adhesive failure is observed at anode attached substrate with bond strengths of 0.16 MPa (control=1.20 MPa).

Example 5

The electrically debondable reactive polyurethane hot melt composition from Example 4 was applied between two aluminum substrates to form a composite.

Upon introduction of 48 V current at 35° C. and 1 atm, adhesive failure is observed at anode attached substrate with bond strengths of 0.12 MPa (control=1.14 MPa).

The invention claimed is:

1. An electrically debondable reactive hot melt adhesive composition, consisting of:
    a) at least one isocyanate-functional polyurethane polymer consisting of the reaction product of at least one polyol selected from the group consisting of polyether polyol, polyester polyol, polycarbonate polyol and mixtures thereof with at least one polyisocyanate, wherein the at least one polyisocyanate is used in an amount such that NCO groups are present in molar excess relative to the hydroxyl groups of the at least one polyol;
    b) at least one organic or inorganic salt;
    c) at least one polar compound comprising an end-capped polyether with no H-acidic functional group; a cyclic carbonate; N,N-dimethylformamide and combinations thereof; and
    d) optionally one or more additives selected from the group consisting of plasticizer, adhesion promoter, pigment, corrosion inhibitor, leveling agent, gloss promoter, stability enhancer, anti-foaming agent, antioxidant and filler, which are different from compounds a) and b).

2. The electrically debondable reactive hot melt adhesive composition according to claim 1, wherein the at least one isocyanate-functional polyurethane polymer is present in an amount of 20% to 90% by weight of the adhesive composition.

3. The electrically debondable reactive hot melt adhesive composition according to claim 1, wherein the at least one organic or inorganic salt is present in an amount of 1% to 30% by weight of the adhesive composition.

4. The electrically debondable reactive hot melt adhesive composition according to claim 1, wherein the at least one polar compound c) is poly(ethylene glycol)bis(2-ethylhexanoate).

5. The electrically debondable reactive hot melt adhesive composition according to claim 1, wherein compound b) is a lithium trifluoromethanesulfonate salt.

6. The electrically debondable reactive hot melt adhesive composition according to claim 1, wherein the free NCO content in the isocyanate-functional polyurethane polymer ranges from 0.1% to 5%.

7. A method for producing an electrically debondable reactive hot melt adhesive composition according to claim 1, the method comprising:
    providing an isocyanate-functional polyurethane hot melt composition optionally comprising one or more additives;

providing an electrolyte composition comprising a suspension, dispersion or solution of at least one organic or inorganic salt in a solvate matrix comprising at least one polar compound; and blending the reactive polyurethane hot melt composition in a molten state with the electrolyte composition, wherein the blending step is performed at temperatures such as to keep the hot melt in the molten state.

8. A method for forming a debondable adhesive bond between a first and a second substrate, the method comprising the steps of:
   i) applying the electrically debondable reactive hot melt adhesive composition according to claim 1 to the surface of the first substrate;
   ii) contacting the first and the second substrates such that a single layer of the electrically debondable reactive hot melt adhesive composition is disposed between the two substrates;
   iii) allowing formation of an adhesive bond between the two substrates to provide bonded substrates; and
   iv) optionally applying a voltage to the bonded substrates whereby adhesion at least one interface between the electrically debondable reactive hot melt adhesive composition and a substrate surface is substantially weakened.

9. The method according to claim 8, wherein
   (1) the voltage applied ranges from 9 to 100 V;
   (2) the voltage is applied for an interval of 1 second to 20 minutes; and/or
   (3) the first and/or the second substrate are electrically conductive.

10. The method according to claim 8, wherein in step iv) in addition to the voltage heating at a temperature up to 80° C. is applied to the bonded substrates.

11. A bonded substrate obtained according to the methods of claim 8, wherein the bonded substrate can be debonded upon application of an electric voltage and, optionally, heat.

12. The electrically debondable reactive hot melt adhesive composition according to claim 1, wherein compound b) is a solid at 25° C.

13. An electrically debondable reactive hot melt adhesive composition, comprising:
    an electrolyte composition;
    a) at least one isocyanate-functional polyurethane polymer;
    wherein the electrolyte composition comprises a suspension, dispersion or solution of b) at least one organic or inorganic salt in a solvate matrix comprising c) at least one polar compound comprising poly(ethylene glycol)bis(2-ethylhexanoate).

14. The electrically debondable reactive hot melt adhesive composition according to claim 13, wherein:
    the at least one organic or inorganic salt comprises Li, Na or K salts of aliphatic $C_{2-6}$ mono- or di-carboxylic acids, Li, Na or K salts of aromatic mono- or di-carboxylic acids or Li, Na or K salts of trifluoromethane sulfonic acids.

15. The electrically debondable reactive hot melt adhesive composition according to claim 13, wherein the at least one polar compound further comprises an end-capped polyether with no H-acidic functional group; a cyclic carbonate; dimethyl sulfoxide; N,N-dimethylformamide and combinations thereof.

16. The electrically debondable reactive hot melt adhesive composition according to claim 13, wherein the isocyanate-functional polyurethane polymer is the reaction product of only at least one polyol and at least one polyisocyanate.

* * * * *